United States Patent
Simon et al.

(10) Patent No.: US 6,861,044 B2
(45) Date of Patent: Mar. 1, 2005

(54) RADIOIODINATED SULFONATED PHENOLS AND PROCESS THEREFORE

(75) Inventors: Jaime Simon, Angleton, TX (US); R. Keith Frank, Lake Jackson, TX (US); Alan D. Strickland, Lake Jackson, TX (US)

(73) Assignee: The Dow Chemical Company, Midland, MI (US)

( * ) Notice: Subject to any disclaimer, the term of this patent is extended or adjusted under 35 U.S.C. 154(b) by 349 days.

(21) Appl. No.: 10/022,885

(22) Filed: Dec. 18, 2001

(65) Prior Publication Data

US 2002/0081662 A1 Jun. 27, 2002

Related U.S. Application Data

(62) Division of application No. 09/671,982, filed on Sep. 28, 2000, which is a division of application No. 09/323,359, filed on Jun. 1, 1999, now Pat. No. 6,315,979.
(60) Provisional application No. 60/087,769, filed on Jun. 2, 1998.

(51) Int. Cl.$^7$ .............................................. A61K 51/00
(52) U.S. Cl. .................................................... 424/1.85
(58) Field of Search .............................. 424/1.85, 1.81, 424/1.89, 1.65; 562/30, 41, 45

(56) References Cited

U.S. PATENT DOCUMENTS

| | | | | |
|---|---|---|---|---|
| 4,574,079 A | * | 3/1986 | Gavras et al. ............. | 424/1.85 |
| 5,163,896 A | | 11/1992 | Suthanthiran .................. | 600/8 |
| 5,393,512 A | | 2/1995 | Vanderheyden ............ | 424/1.53 |
| 5,429,582 A | | 7/1995 | Williams ......................... | 600/2 |
| 5,611,767 A | | 3/1997 | Williams ........................ | 600/2 |

FOREIGN PATENT DOCUMENTS

| | | | |
|---|---|---|---|
| DE | DT-139918 | * 4/1975 | |
| WO | 98/55154 | 12/1998 | ......... A61K/51/087 |

OTHER PUBLICATIONS

Wahl, R.; Bohner, J.; Kallee. E. Nucl. Med. Suppl. (1973), No. 11, p. 179–83 (German plus translation).
Wahl, R.; Bohner, Jurgen; et al. Arzneim.–Forsch (1973), 23(8), p. 1009–14 (German plus translation).
De Wit. Peter; Woldhuis, Alex F.; Cerfontain, Hans; Lab. Org. Chem. U of Amsterdam; Racl. Trav. Chim. Pays–Bas 107, 668–675 (1988).
Phillip, Manfred; Fresenius J. Anal. Chem (1998), 360(2), p. 184–191.
Krummeich C. et al. "Convenient Direct NCA Electrophilic Radioiodination of Arenes using Iodo–gene<TM" Applied Radiation and Isotopes, vol. 47, No. 5, May 6, 1996, pp. 489–495.
Krummeich C. et al. "Kit preparation of n.c.a. 3–"[$^{123}$] Iodo–L–α–methyltyrosine [$^{123}$I]IMT, 3–[$^{123}$I]Iodo–O–methyl–L–tyrosine [$^{123}$I]OMIT and 3–[$^{123}$I]Iodo–O–methyl–L–α–methyltyrosine [$^{123}$I]OMIMT Using Sep–Pak™ C–18 Cartridges, appl. Radiar. Isol. vol. 46, No. 9, pp. 917–6921, 1995.
Krummeich C. et al. "Synthesis and Biodistribution of Radioiodinated Amino acids: A Comparative Evaluation" Journal of Nucl. Med. vol. 3, No. 5 Suppl., pp. 94, 1994.

* cited by examiner

*Primary Examiner*—Michael G. Hartley

(57) ABSTRACT

The present invention concerns the use of a radioiodinated phenolic compound of the formula

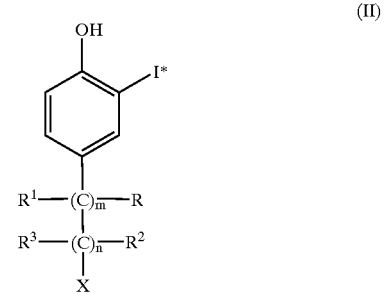

(II)

wherein: m and n are independently 0, 1, 2 or 3, X is a group that is negatively or positively charged at physiological pH, R, R$^1$, R$^2$ and R$^3$ are independently hydrogen, C$_1$–C$_4$ alkyl, or a carboxyl group, and I* is $^{123}$I, $^{131}$I or $^{125}$I, and its pharmaceutically-acceptable salts. The compound is formulated and used in vivo in an animal in brachytherapy in an implantable catheter. In addition, due to the rapid renal clearance of these compounds, they may be used to study renal function. A process to prepare these compounds is also disclosed.

11 Claims, 2 Drawing Sheets

Iodide

I-HBS

RADIOIODINATED SULFONATED PHENOLS AND PROCESS THEREFORE

CROSS REFERENCE STATEMENT

This is a divisional application of U.S. Ser. No. 09/671,982, filed Sep. 28, 2000, now pending, which is a divisional of U.S. Ser. No. 09/323,359, filed Jun. 1, 1999, now issued as U.S. Pat. No. 6,315,979, which claims benefit of U.S. Provisional Application No. 60/087,769, filed Jun. 2, 1998, now abandoned.

FIELD OF THE INVENTION

The present invention relates to a radioactive fluid used to treat tumors in vivo in an animal body. The fluid is to be used in combination with an implantable catheter attached to an inflatable balloon that is placed in proximity of a tumor or in the cavity left by the surgical removal of a tumor from an animal body. The radioactive fluid of this invention is used to inflate the balloon and provide a radiation dose to tumor tissue or to tissue surrounding the resection cavity. This solution is a "brachytherapy fluid" that consists of an aqueous solution of a water-soluble radioactive molecule with other appropriate physiologically-acceptable ingredients.

BACKGROUND OF THE INVENTION

In many cases, surgical procedures for the removal of a tumor leaves cancer cells in the area adjacent to the tumor. This occurs for various reasons, for examples, the cancer cells are not visible to the surgeon's view or no dye or stain is available to enable the cancer cells to be seen by the surgeon. These remaining cells can cause recurrence of the cancer. Additional therapies are thus needed to treat this surgical area.

One form of treatment is to give a local radiation dose to this area. This can be accomplished by brachytherapy, which involves the implantation of a radioactive source (as solid pellets) in an area near or surrounding a tumor. Traditional brachytherapy involves placing one or more solid radioactive pellets or needles in the area to be treated. Determining proper placement of the radioactive pellets is not simple and the implantation itself is difficult, expensive, time consuming and offers a potential for the introduction of infection. Additionally, dosimetry for these sources is often difficult to calculate because of complex geometry issues.

U.S. Pat. No. 5,429,582 teaches the use of an implantable apparatus, such as a catheter, for the treatment of tissue surrounding a cavity left by surgical removal of a brain tumor. This technique has the advantage over traditional brachytherapy in that the apparatus is inserted during the same surgical procedure used to remove the tumor; thus no additional surgery is required and the possibility of infection is greatly reduced. Additionally, the balloon fills the volume left by the tumor mass and the determination of where to place the radioactivity is less complicated. Dosimetry calculations are also simplified with a single, spherical radioactive source. In addition, U.S. Pat. No. 5,611,767 teaches the method and apparatus for radiation treatment of a tumor using an inflatable treatment device placed in an incision adjacent to the tumor wherein the inflatable device is filled with a radioactive treatment fluid. However, a description of the radioactive solution to be used with the device is not included in these above patents.

Several radioactive isotopes of iodine have been used for medical applications. Some of these isotopes include iodine-123 ($^{123}$I), iodine-125 ($^{125}$I), and iodine-131($^{131}$I). Iodine-123 has a 13.1 hour half life and emits gamma photons that are useful for nuclear medicine imaging. Iodine-125 has a 60.14 day half life and emits several relatively low energy photons that are used as labels on antibodies to guide surgical procedures in cancer patients and as a tracer to evaluate kidney function. Iodine-131 has a 8.04 day half life and emits gamma photons that are useful for nuclear medicine imaging plus beta particles useful for therapeutic applications.

Much work has been done on radioiodination methods. Molecules of interest have generally been proteins such as antibodies, smaller peptides, and other biologically active molecules. For example, the dye—tetraiodotetrachlorofluorescein (rose bengal)—has been labeled with $^{131}$I to study liver function [Taplin, G. V., et al., *J. Lab. Clin. Med.*, 45, 665 (1955)]. Alpha-methyltyrosine iodinated with $^{123}$I can be used to assess amino acid transport rate in gliomas [Kuwert, T., et al., *J. Nuclear Medicine* 38(10), 1551 (1997)]. Also, $^{125}$I labeled monoclonal antibodies have been used to help identify cancer tissue during surgical procedures [Nieroda, C. A., et al., *Cancer Res.*, 55(13), 2858–65 (1995)].

A process for radioiodination of molecules is usually accomplished by either an exchange reaction or an electrophilic substitution. For example, sodium iothalamate is labeled with $^{125}$I in an exchange reaction by heating radioactive sodium iodide (e.g., Na$^{125}$I) with iothalamate [Hung, Joseph C., et al., *Nucl. Med. Biol.*, 21(7), 1011–12 (1994)]. The electrophilic process is facilitated by the oxidation of iodide to an electrophile in the presence of the molecule to be labeled. Electrophilic attack can then occur, typically at the ortho position of phenolic groups, such as tyrosine. Several common oxidizing agents are commercially available, for example from Pierce Chemical Company, PO Box 117, Rockford, Ill. 61705, US. Chloramine-T (N-chloro-4-methylbenzenesulfonamide sodium salt, Pierce Chemical Company) is a water soluble oxidizing agent. It requires the addition of an another reagent to stop the reaction and must then be separated from the solution. IODO-GEN® (Pierce Chemical Company) is a water-insoluble oxidizing agent for iodination. It is typically coated as a film on the inside of the reaction vessel. This is accomplished by dissolving it in chloroform, applying the solution to a reaction tube, then evaporating the solvent. Iodination is accomplished by addition of an aqueous solution containing the radioactive iodide and the material to be labeled to the IODO-GEN®-coated test tube. Removing the solution from the tube terminates the reaction and effects separation of the substrate from the reagent. Another popular method involves the use of IODO-BEADS® (Pierce Chemical Company) which are polystyrene beads with the oxidizing agent (Chloramine-T) chemically bonded to the bead. Removing the plastic beads from solution terminates the reaction.

The structures of these oxidizing agents are shown below:

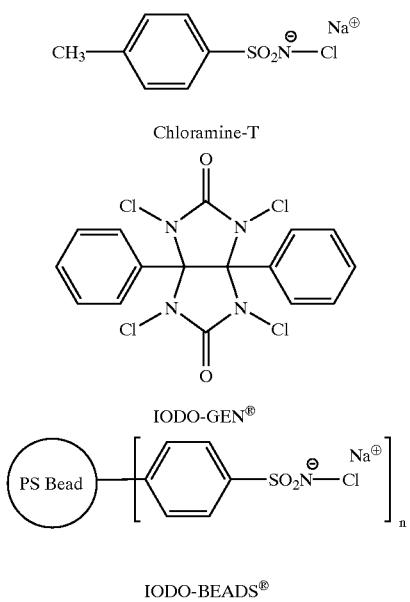

Chloramine-T

IODO-GEN®

IODO-BEADS®

Most commonly, the above reagents are used to radiolabel proteins. The amino acid most reactive towards electrophilic iodination is tyro sine because of the phenolic group. Scheme 1 below illustrates the radioiodination of tyro sine using IODO-GEN® as the oxidizing agent. Iodide is oxidized to an electrophilic species, postulated to be I-Cl. Electrophilic attack then occurs at the ortho position of the phenol.

Scheme 1
Iodination of Tyrosine

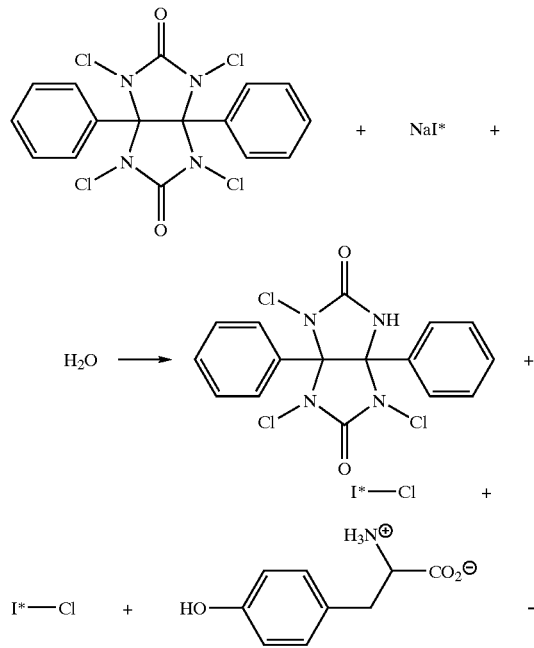

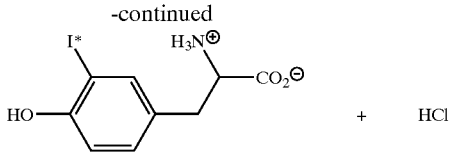

+ HCl

Although iodine-125 has ideal nuclear properties for use in the above described devices, in the iodide form $^{125}I$ has less than ideal properties. For example, it is readily oxidized to form volatile iodine, $I_2$. In addition, if leakage from the device occurs, activity will concentrate, in body tissues, such as thyroid and stomach, giving an undesirable radiation dose to those tissues for the patient. Thus, although technology exists for the iodination of many molecules, no one has described the properties and compounds to be used with said implantable devices described above. There is thus a need for a compound that has the appropriate properties for use with these devices.

SUMMARY OF THE INVENTION

This invention provides a radioactive solution to be used in conjunction with the implantable apparatus described in U.S. Pat. Nos. 5,429,582 and 5,611,767 and still have the solution clear from the body if leakage should occur without undesirable concentration of radioactivity in any tissue. Surprisingly, it has been found that radioiodinated compounds meet these desired properties are compounds of the formula

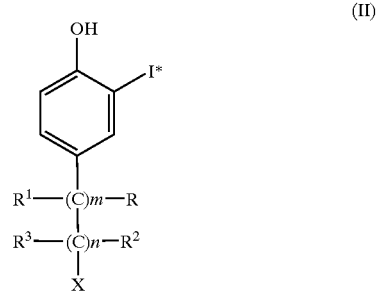

(II)

m and n are independently 0, 1, 2 or 3, X is a group that is negatively or positively charged at physiological pH, R, $R^1$, $R^2$ and $R^3$ are independently hydrogen, $C_1$–$C_4$ alkyl, or a carboxyl group, and I* is $^{123}I$, $^{131}I$ or $^{125}I$, and its pharmaceutically-acceptable salts.

A method for using these radioiodinated compounds of Formula (II) in a catheter for treating the tissue around a tumor cavity after removal of the tumor, especially in vivo in the brain, is described. A formulation for using these compounds of Formula (II) as a physiological solution is described. These compounds are formulated to be physiologically-acceptable, and may have a radiolytic protectant present. The compound is formulated and used in vivo in an animal in brachytherapy in an implantable catheter.

In addition, due to the rapid renal clearance of the compounds of Formula (II), they may be used to study kidney function.

A process for preparing a compound of Formula (II) comprises radioiodinating a compound of Formula (I)

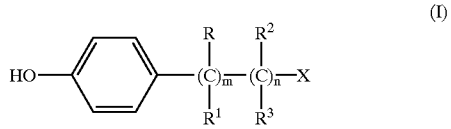

wherein: m, n, X, R, $R^1$, $R^2$ and $R^3$ are as defined above, with an radioiodinating agent, under these conditions a small amount of the radioactivity may be as the bisiodinated compound of the formula

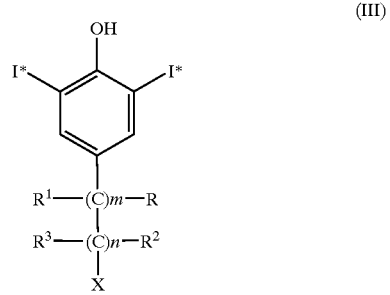

wherein: m, n, X, R, $R^1$, $R^2$, $R^3$ and I* are as defined as above.

The process to prepare the compounds of Formula (II) is also provided so that minimum exposure to the radiation is provided during preparation while providing high yield and purity; less than 15%, preferably less than 10%, of unbound iodine is present at the end of the iodination reaction. Upon completion of the radioiodination reaction any unbound iodide is further reduced to less than 5%, preferably less than 3%, in the final solution.

DETAILED DESCRIPTION OF THE INVENTION

Figure 1:
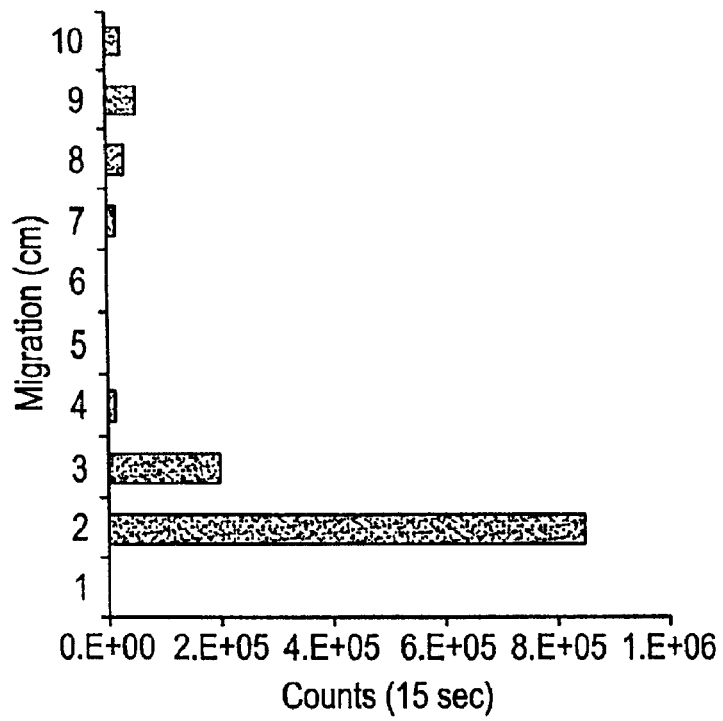
FIG. 1 is the graphic representation of the NaI data from Table 1.

This invention provides a radioactive solution to be used in conjunction with the implantable apparatus described in U.S. Pat. Nos. 5,429,582 and 5,611,767. When the balloon apparatus is filled with the radioactive solution of this invention, it provides a radiation dose to the area surrounding the balloon without giving significant dose to other areas of the body or to those personnel handling the radioactive solution. In case of leakage of the radioactive solution, it is desirable for the radioactivity to be rapidly excreted from the body without significant uptake in any tissue. In addition, it is an object of this invention for the radioactive solution to be easily prepared in high yields. It is a further object of this invention to provide a means to remove the radioactive components from the solution after the solution is removed from the device. This latter aspect of the invention helps with waste disposal of the radioactive component after it is used in an animal, including a human patient.

It is another advantage of this invention to provide compounds for the study of renal function. Several radiopharmaceuticals have been used to study the kidneys, particularly compounds that have some retention in the kidneys were used for imaging studies. For example, in 1960 radioactive mercury compounds were used to image the kidneys [McAfee, J. G., et al., "Comparison of renal extraction efficiencies for radioactive agents in the normal dog", J. Nucl. Med,. 22, 333 (1981)]. Later a series of $^{99m}$Tc agents were used for the same purpose [Chervu, L. R., et al., "Renal radiopharmaceuticals—An update," Semin. Nucl. Med. 12, 224 (1982)]. A second class of compounds was used to study renal function. These compounds are cleared by the kidneys with little to no retention. Examples include iothalamate labeled with $^{125}$I, $^{99m}$Tc-DTPA [Barbour, G. L., et al., "Comparison of inulin, iothalamate, and $^{99m}$Tc-DTPA for measurement of glomerular filtration rate," J. Nucl. Med. 17, 317 (1976)], ortho-$^{131}$I-iodohippurate [Tubis, M., et al., "preparation and use of $^{131}$I-hippurate in kidney function tests," Proc. Soc. Exp. Biol. Med. 103, 497 (1960)], and $^{99m}$Tc-DADS [Fritzberg, A. R., et al., "Chemical and biological studies of Tc-99m N,N'-bis(mercapto acetamido) ethylenediamine: a potential replacement for I-131-iodohippurate," J. Nucl. Med. 22, 28 (1981)].

The radioactive solution of this invention consists of an aqueous solution of a water soluble phenolic compound that is labeled with iodine, especially $^{125}$I. The compound to be labeled with radioactive iodine has the general formula below:

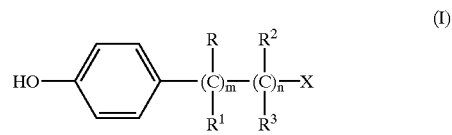

wherein: m and n are independently 0, 1, 2 or 3, X is a group that is negatively or positively charged at physiological pH, and R, $R^1$, $R^2$ and $R^3$ are independently hydrogen, $C_1$–$C_4$ alkyl, or a carboxyl group. Examples of X groups are primary amines, substituted amines which may be secondary, tertiary, or quaternary, or sulfonates. The sulfonates are particularly preferred. At physiological pH (~7.4) sulphonic acid groups will be deprotonated to give a negative charge, while the amines would be protonated giving a positive charge.

Some preferred examples of compounds of Formula (I) are shown below:

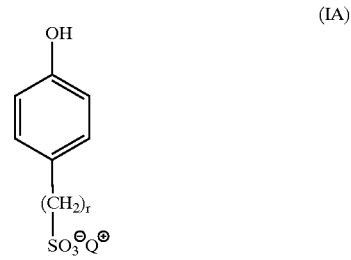

-continued

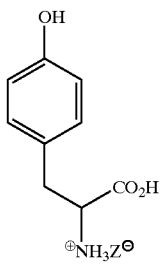
(IB)

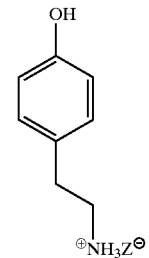
(IC)

wherein: Q and Z includes any suitable pharmaceutically-acceptable salt, for example, when Q is present then the salt is alkali metal ions such as sodium or potassium, or ammonium ion, and r is 0, 1 or 2; when Z is present then the salt is chloride or bromide. The preferred compound of Formula (IA) is when r is 0, Q is sodium, and named as sodium 4-hydroxybenzenesulfonate ("HBS"). At physiological pH (~7.4) sulphonic acid groups will be deprotonated to give a negative charge. Formula (IB) is tyrosine and Formula (IC) is tyramine, both having the amine protonated at physiological pH with a suitable pharmaceutically-acceptable salt as an anion, such as chloride or bromide.

The compounds of Formula (I) are easily radioiodinated in high yields using previously described techniques to provide a compound of the formula below:

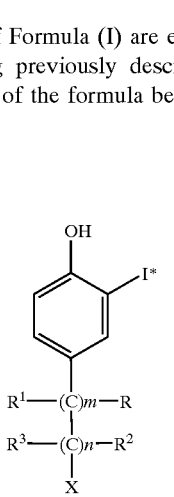
(II)

wherein: m, n, R, $R^1$, $R^2$, $R^3$ and X are defined as for Formula (I) above, and I* is $^{123}$I, $^{131}$I, or $^{125}$I. The Formulas (IA), (IB) and (IC) are also iodinated in the same manner to provide the corresponding compounds of Formulas (IIA), (IIB) and (IIC).

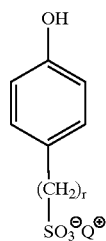
(IA)

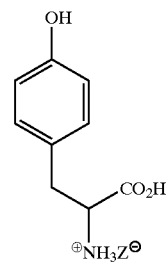
(IB)

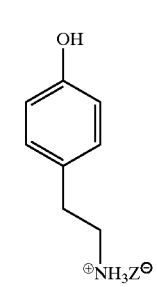
(IC)

The formulations of the above compounds of Formula (II) with suitable pharmaceutically-acceptable carriers is a part of this invention. The formulation must be in a liquid form to be used in the balloon catheter and be physiologically acceptable in the event that the liquid may come in contact with tissue in the animal during use. The liquid may be a solution, emulsion, or suspension in a physiologically-acceptable form. Examples of preferred carriers are aqueous solutions e.g., buffers such as phosphate or HEPES adjusted to physiological pH. It is important that the compound be in solution with no solids present. The amount of radioactive compound present in the formulation depends upon which iodine isotope is used, the desired dose, the balloon volume, and the contact time. For example, for $^{125}$I with about a one week contact time in a device of U.S. Pat. No. 5,429,582, the desired activity is from about 20 to about 1000 mCi, preferably 50 to about 500 mCi.

Although Chemical Abstracts lists registry number 121208-93-3 as 4-hydroxy-3-iodobenzenesulfonic acid, this compound is not radioactive and has no given utility. Also a kinetic study was done by P. De Witt et al., *Neth. Rec. Trav. Chim. Pays-Bas*, 107(12), 668–75 (1988) but no radioactive molecule or utility was given. Thus the literature does not discuss the compounds of Formula (II) or their use.

The effect of the diiodophenolsulphonic acid (or 3,5-diiodo-4-hydroxybenzenesulphonic acid or sozoiodolic acid) on thyroid hormones was discussed by R. Wahl et al., *Nucl.-Med., Suppl.* 11, 179–83 (1973). They found that diiodophenolsulphonic acid at concentrations up to 0.2 mM did not displace triiodothyronine from its thyroxine-binding globulin and albumin, but did selectively display thyroxine from prealbumin-binding sites. Thus the effect of diiodophenolsulphonic acid on thyroid hormones was minimal.

The use of 3,5-diiodo-4-hydroxybenzenesulphonic acid as an X-ray contrast agent and as a disinfectant is discussed by R. Wahl et al., *Arzneim.-Forsch.* 23(8), 1009–14 (1973). The article focus is on the diiodo compound and its effect on thyroid hormones. The process for preparing the diiodo compound also produced the mono-iodo compound ($^{125}$I-iodophenolsulphonate) which was separated but not tested nor any utility given. No toxic effects were found with the diiodo compound.

To purify the final radioactive solution, after the iodination reaction is completed by any of the known methods described above, residual unbound iodine is converted to iodide (I$^-$) by use of a reducing agent such as metabisulfite or thiosulfate. Iodide in the solution is then removed by precipitation with silver ions. Addition of silver can be accomplished by using a water-soluble silver salt, such as silver nitrate, or by passing the solution through a cation exchange resin in the silver form. The solution can then be passed through a cation exchange resin in the sodium form to remove residual silver. After the silver precipitation the solids can then be removed from the solution by filtration. To prevent radiolysis of the radioactive solution prior to use, it can be frozen and/or radioprotectants are used, such as benzyl alcohol, ascorbic acid, gentisic acid, cysteine, butylated hydroxytoluene ("BHT"), citric acid, human serum albumin ("HSA"), glycerol, cysteamine, sulfarem, glutathione, tryptophan, and iodoacetamide.

In addition to the compounds of Formula (II) above, it is believed that small amounts of the bis-iodinated compounds could be formed. The structure of these compounds is shown below:

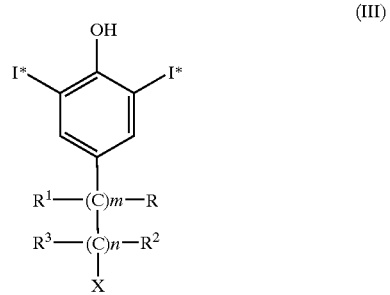

(III)

Wherein: m, n, R, R$^1$, R$^2$, R$^3$ and X are defined as in Formula (I) above, and I* is defined as in Formula (II) above. If desired, the amount of bis-iodinated compound can be minimized by using a large excess of starting material over iodide. Additionally, the mono-iodinated compound could be separated from excess starting material and bis-iodinated compound by using standard chromatographic techniques.

It has now been found that the best mode for making the present radioactive solutions of Formula (II) occurs when an apparatus is used as described in our copending application U.S. Ser. No. 09/323673, filed on even date herewith, and entitled "Apparatus for the Preparation of Radioactive Solutions" having Attorney docket no 44191A, and inventors of R. Keith Frank and Jaime Simón, particularly FIG. 5 thereof with its discussion, the disclosure of which is hereby incorporated by reference.

Figure 3:
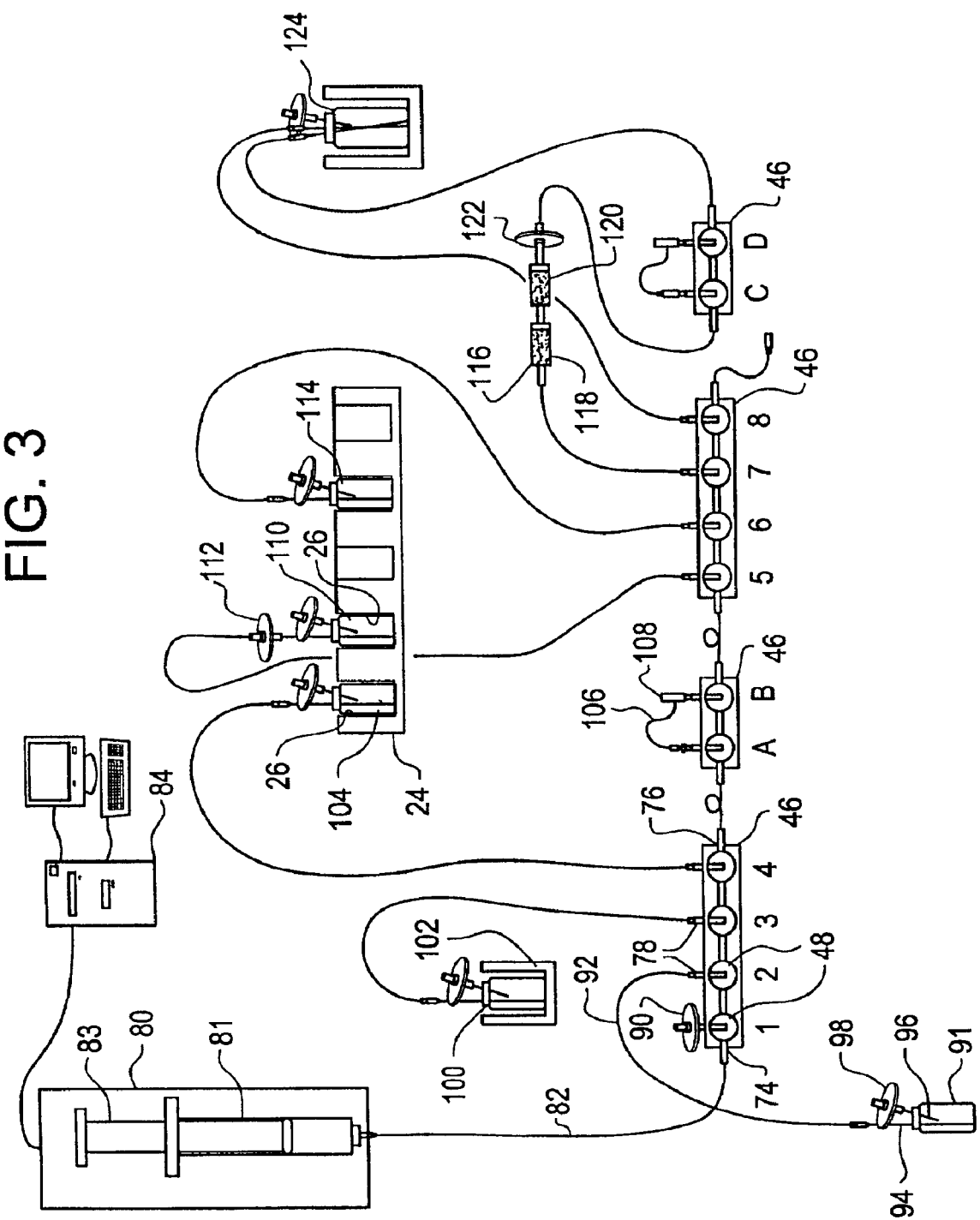
FIG. 3 is a schematic diagram of the apparatus that may be used to prepare the radioiodinated compounds of Formula (II).

An apparatus has been used to prepare the radioactive compounds of Formula (II) where a plastic housing that has a reagent support adapted to receive a plurality of radiation-shielded vials, which vials are pivotally mounted to allow agitation or inverting of the vials. The apparatus also includes a series of valve manifolds secured within the housing and connected by plastic tubing with the vials to ensure proper routing of the reagent within the housing. A computer controlled syringe pump is used to transfer the solution between reagent vials and to dispense the reagents. The computer controls both the syringe pump and prompts an operator, where necessary, for any manual operations to conduct the process. A schematic diagram is provided of this apparatus as FIG. 3. Optionally, computer controlled valves may be used.

When iodinated with radioactive iodine, the compounds of Formula (II) are water soluble. When introduced into the bloodstream of an animal, the iodinated compounds of Formula (II) are readily cleared from the body via the renal system and are expected to have low toxicity.

Compounds of Formula (II) may also be lyophilized for storage or transport. To maintain physiological pH (~7.4) suitable buffers are used such as bicarbonate, phosphate, HEPES, or other known suitable buffers. A radiolytic protectant can be used as mentioned above. The pH of the solution can range from about 5 to about 9, preferably from about 6.5 to about 8.5, but physiological pH is most preferred from about 7 to about 8.

The amount of radioactive solution used for therapeutic applications depends upon several factors, such as which iodine isotope, the size of the resected area to be treated, the contact time, and dose of radioactivity desired. An effective amount of the $^{125}$I-labeled solution for therapeutic uses in devices taught in U.S. Pat. No. 5,429,582 is in the range from about 50 to about 500 mCi, preferably from about 100 to about 200 mCi, and more preferably about 150 mCi per dose.

The formulation is injected into the implanted catheter and the solution left in the device for the desired treatment period. The solution is then removed by syringe and the deflated catheter removed.

The following definitions are used in the specification and examples below.

cm=centimeter mCi=milliCurie;

the conversion factor to IUPAC units is 1 mCi=37 MBq

μL=microliter mm=millimeter mL=milliliter mg=milligram g=gram

HBS=sodium 4-hydroxybenzenesulfonate dihydrate

HEPES=N-2-hydroxyethylpiperazine-N'-2-ethanesulfonic acid

The invention will be further clarified by a consideration of the following examples, which are intended to be purely exemplary of the present invention.

EXAMPLE 1

A 1 cm×10 cm paper strip was spotted with 2 μL of $^{131}$I sodium iodide solution at the center of the second cm section. The strip was placed in a container with a small volume of 0.1M silver nitrate solution such that about the first 50 mm of the strip was below the liquid level. The strip was left in place until the liquid wicked to the top of the paper strip. The strip was then cut into 1 cm sections and each section counted on a thallium-drifted sodium iodide detector coupled to a multi-channel analyzer.

IODO-GEN® (2 mg, Pierce Chemical Company) was dissolved in 1 mL of chloroform and the solvent was evaporated by passing an argon stream into the vial while rotating it. The solid IODO-GEN® was thus deposited as a film on the sides of the vial. A solution containing 25 mg of HBS in HEPES buffer (pH=7.5) and tracer amounts of radioactive sodium iodide ($^{131}$I) was added to the vial. After 30 minutes, a 6 μL sample of this solution was spotted on an 10 cm paper strip and eluted with 0.1N silver nitrate as described above. A comparison on the activity in the strips for the NaI and the sodium iodide reacted with HBS ($^{131}$I-HBS) is given in Table 1 below.

TABLE 1

Counts in Paper Chromatography Cut in 1 cm Sections
(Bottom of Strip is Section 1)

| Section | Na$^{131}$I | $^{131}$I-HBS |
|---|---|---|
| 1 | 6374 | 26 |
| 2 | 847941 | 901 |
| 3 | 195459 | 208 |
| 4 | 7237 | 57 |
| 5 | 4956 | 94 |
| 6 | 5212 | 280 |
| 7 | 8450 | 1446 |
| 8 | 24258 | 3672 |
| 9 | 47656 | 8478 |
| 10 | 15505 | 2702 |

Figure 2:
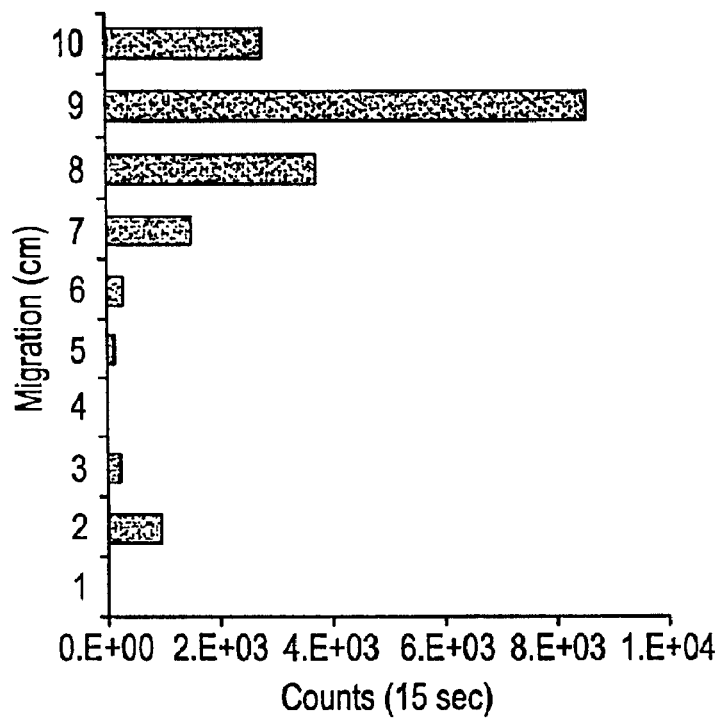
FIG. 2 is the graphic representation of the $^{131}$I-HBS data from Table 1.

This data (plotted in FIGS. 1 and 2) shows that radioactive sodium iodide does not move up the strip while the radioactivity in the reaction mixture moves up the strip. This is consistent with the formation of iodinated HBS (I-HBS) with about 7% unbound iodide, (I$^-$).

EXAMPLE 2

Samples of radioactive ($^{131}$I) NaI and iodinated HBS ($^{131}$I-HBS), prepared as described in Example 1, were analyzed by paper electrophoresis. Thus 2–10 μL samples were spotted at the center of 33 cm paper strips (Whatman 1 Chromatography Paper) after wetting with an electrophoresis buffer at pH 8.6. A potential of 500 V was applied for 15 minutes. The strips were cut into 1 cm sections and counted as in Example 1. The results show the radioactivity in the sodium iodide sample migrating as an anion 7 to 8 cm. The I-HBS migrated 4 cm. A mixture of the two solutions showed that separation of NaI from I-HBS was possible.

EXAMPLE 3

Two mg of IODO-GEN® dissolved in one mL of chloroform was placed in a glass vial. The vial was rotated at an angle while allowing the solvent to evaporate and deposit the reagent as a film on the sides of the vial. A quantity of 25 mg of HBS was weighed into a second vial. To the second vial was added one mL of a solution containing 0.28 mg of carrier Na$^{127}$I and tracer amounts of radioactive Na$^{131}$I plus 5 mL of HEPES buffer (0.02 M, pH=7.5). The contents of the second vial was transferred to the first (IODO-GEN®) vial using a pipette. The paper chromatography method described in Example 1 was used to analyze the solution at 5, 8, 12, and 16 minutes after introduction into the IODO-GEN® vial. The percentage of the activity bound to HBS (moving with the solvent front) was 64, 84, 94 and 94%, respectively. In other words, there was about 6% unbound iodide. After 20 minutes, the contents of the IODO-GEN® vial were transferred into a vial containing one mg of sodium metabisulfite. Analysis by paper chromatography of the solution exposed to metabisulfite showed 94% of the iodine bound to HBS. The solution was then passed through a cation exchange resin in the silver form, followed by a cation exchange resin in the sodium form, and lastly through a 0.2 micron filter. Analysis by paper chromatography after passing through the columns and filter showed 97% of the radioactivity bound to HBS, similarly there was about 3% unbound iodide.

Additionally, the purified solution was analyzed by both reversed-phase HPLC and ion chromatography. Results in both cases showed a single radiometric peak corresponding to mono-I-HBS.

EXAMPLE 4

The radioiodinated HBS ($^{131}$I-HBS) solution (100 μL), prepared in Example 3, was injected with of into a tail vein of three Sprague-Dawley rats (180–220 g). After one hour, the animals were sacrificed and the tissues and organs of interest were removed and weighed. The amount of radioactivity in each organ was determined by counting the tissue sample with a sodium iodide detector coupled to a multi-channel analyzer. The counts in the tissues were compared to the average counts of three 100 μL aliquots of $^{131}$I-HBS counted in the same manner. The percentage of dose in the bone was calculated by assuming the femur to represent $\frac{1}{25}$ the weight of the total skeletal system. The blood dose was calculated by assuming that blood comprises 6.5% of the total body weight. Muscle dose was calculated by assuming that muscle comprises 43% of the total body weight. The results of this biodistribution experiment are shown in Table 2 below.

TABLE 2

Percent Injected Dose $^{131}$I-HBS
1 Hour After Injection

| Organ | Rat 1 | Rat 2 | Rat 3 | Average | σ |
|---|---|---|---|---|---|
| Bone | — | 0.37 | 0.16 | 1.00 | 0.90 |
| Tail | 0.01 | 0.16 | 0.09 | 0.08 | 0.05 |
| Liver | 0.05 | 0.08 | 0.06 | 0.06 | 0.01 |
| Kidney | 0.19 | 0.10 | 0.08 | 0.12 | 0.04 |
| Spleen | 0.01 | 0.00 | 0.01 | 0.00 | 0.00 |
| Muscle | 0.88 | 0.38 | 0.05 | 0.40 | 0.30 |
| Blood | 0.14 | 0.18 | 0.15 | 0.16 | 0.01 |
| Heart | 0.01 | 0.01 | 0.02 | 0.01 | 0.01 |
| Lung | 0.01 | 0.03 | 0.02 | 0.02 | 0.01 |
| Thyroid | 0.00 | 0.00 | 0.00 | 0.00 | 0.00 |
| Stomach | 0.33 | 0.31 | 0.24 | 0.29 | 0.03 |
| Sm Int. | 1.51 | 0.67 | 1.24 | 1.10 | 0.30 |
| Lg. Int. | 0.08 | 0.12 | 0.05 | 0.08 | 0.02 |

These results show that very little activity was found in the body 1 hour post injection. Almost all the activity was in the urine for all the animal. The lack of activity in the thyroid implies that there is little to no iodide (I$^-$) in the solution.

EXAMPLE 5

An I-HBS solution was prepared as in Example 3. Twenty μL of this solution was injected intrathecally in two Sprague-Dawley rats (100–150 g). After two hours the rats were sacrificed and dissected. The amount of radio activity in various organs and tissues was determined as in Example 4. The results (average of two rats) are listed in Table 3.

TABLE 3

Two Hour Rat Biodistribution after Intrathecal Administration

| Tissue | % Injected Dose | s.d. |
|---|---|---|
| Bone | 1.3 | 0.6 |
| Liver | 0.2 | 0.1 |
| Kidney | 0.3 | 0.2 |
| Spleen | 0.0 | 0.0 |
| Muscle | 0.5 | 0.5 |
| Blood | 0.7 | 0.5 |
| Heart | 0.0 | 0.0 |
| Lung | 0.0 | 0.0 |
| Brain | 1.6 | 1.0 |
| Thyroid | 0.0 | 0.0 |
| Stomach | 0.3 | 0.0 |
| Sm. Intestine | 0.5 | 0.2 |
| Caecum | 0.0 | 0.0 |
| Colon | 0.9 | 1.2 |
| Bladder | 0.3 | 0.4 |
| Urine* | 88 | 2 |

*Recovery of urine may have been less than quantitative.

These results show that the radioactivity had cleared the kidney and little or no radioactivity was present in the thyroid.

EXAMPLE 6

A quantity of 5 mg of tyramine was weighed into a glass vial. To the vial was added 1 mL of potassium biphthalate—sodium hydroxide buffer (0.05M, pH 5). The contents of this vial were transferred by pipette to an IODO-GEN® vial prepared as in Example 3. Tracer amounts of radioactive $Na^{131}I$ were added. The paper chromatography method described in Example 1 was used to analyze the solution after 7 minutes and the percentage of the activity bound to tyramine was 94%. In other words, the free iodide was about 6%. The contents of the IODO-GEN® vial were then transferred into a vial containing 1 mg of sodium metabisulfite. Analysis by paper chromatography of the solution exposed to metabisulfite was 92%. The solution was then passed through an anion exchange resin followed by a 0.2 micron filter. Analysis by paper chromatography after passing through the columns and filter was 98%, or about 2% free iodide.

EXAMPLE 7

The biodistribution of the radioiodinated tyramine prepared in Example 6 was determined as in Example 4 (using 2 rats). The results are shown in Table 4.

| Organ | Rat 1 | Rat 2 | Average | σ |
|---|---|---|---|---|
| Bone | 0.30 | 0.20 | 0.25 | 0.07 |
| Tail | 0.77 | 0.20 | 0.49 | 0.40 |
| Liver | 0.46 | 0.57 | 0.52 | 0.08 |
| Kidney | 0.26 | 0.25 | 0.26 | 0.00 |
| Spleen | 0.01 | 0.01 | 0.01 | 0.00 |
| Muscle | 1.31 | 0.87 | 1.09 | 0.31 |
| Blood | 1.19 | 1.06 | 1.13 | 0.09 |
| Heart | 0.03 | 0.02 | 0.03 | 0.01 |
| Lung | 0.03 | 0.26 | 0.15 | 0.16 |
| Thyroid | 0.12 | 0.07 | 0.09 | 0.04 |
| Stomach | 0.37 | 0.48 | 0.43 | 0.07 |
| Sm. Int. | 3.47 | 4.67 | 4.07 | 0.85 |
| Lg. Int. | 0.46 | 2.02 | 1.24 | 1.10 |

These results show that most radioactivity had cleared the body 1 hour post injection. There was very little in the thyroid implying that there is very little iodide ($I^-$) in the solution.

EXAMPLE 8

Neurotoxicology tests were run on rats in order to determine the effect of gross leakage of I-HBS on neurological function. Three treatment groups of 10 rats each were tested: one group was a control group injected intrathecally with saline, and two groups were injected intrathecally with two concentrations of cold (non-radioactive) I-HBS. At injection the average weight of the rats was 100 g.

A cold (I-HBS solution was prepared which contained the following:

| Ingredient | mM |
|---|---|
| Sodium ascorbate | 252.39 |
| Sodium acetate | 12.19 |
| HEPES | 31.47 |
| HBS, Na | 5.31 |
| I-HBS, Na | 0.067 |

He prepared cold I-HBS solution was then subjected to a radiation dose of from 20.4 to 21.3 kGy. This was done in order to simulate radiolytic degradation that would occur in an $^{125}$I-HBS formulation under prolonged time lapse.

The dose of I-HBS formulation for patients with an implanted balloon catheter would be about 0.043 mL per kg of body weight. For a 100 g rat a dose of about 4.3 μL would be equivalent. Test group rats were injected with roughly 2× (10 μL) and 4× (20 μL) this dose level. The total injection volume was kept at 20 μL by dilution with physiological saline.

The rats of each group were anesthetized by injecting 2.5 μL/kg intramuscularly a mixture of 20 mg ketamine hydrochloride and 0.15 mg xylazine per mL.

Group 1 rats were injected with 20 μL of physiological saline.

Group 2 rats were injected with 10 μL of the cold I-HBS formulation mixed with 10 μL of saline. This simulates a gross leakage of roughly twice a normal dose into the brain of a patient.

Group 3 rats were injected with 20 μL the cold I-HBS formulation. This simulates a gross leakage of roughly four times a normal dose into the brain of a patient.

The results were evaluated according to the procedure published in Carrillo, et al., "Prolonged severe hemorrhagic shock and resuscitation in rats does not cause subtle brain damage." *J. Trauma: Injury, Infection, and Critical Care*, 45, 239–249 (1998). The results showed that no rats had abnormal neurological scores. Because this neurological test is quite sensitive it is expected that no neurological damage wold be shown when using less degraded iodinated solutions, such as those described in prior examples.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A pharmaceutical formulation comprising as an active ingredient a radioiodinated compound of the formula

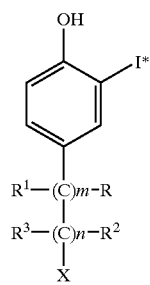
(II)

wherein: m and n are independently 0, 1, 2 or 3, X is a sulfonate, R, $R^1$, $R^2$ and $R^3$ are independently hydrogen, $C_1$–$C_4$ alkyl, or a carboxyl group, and I* is $^{123}$I, $^{131}$I or $^{125}$I, and its pharmaceutically-acceptable salts, with a pharmaceutically-acceptable carrier, having less than about 15% of unbound iodine present.

2. The formulation of claim 1 wherein the formula groups m and n are 0, R, $R^1$, $R^2$, and $R^3$ are hydrogen, and X is a sulfonate, as its pharmaceutically-acceptable salt.

3. The formulation of claim 2 which has as its active ingredient a compound that is sodium 3-iodo-4-hydroxybenzenesulfonate.

4. The formulation of claim 1 where the formula term I* is $^{125}$I.

5. The formulation of claim 1 wherein the formulation has as its pharmaceutically-acceptable carrier water that is buffered to physiological pH.

6. The formulation of claim 5 wherein the buffer is HEPES and the pH is from 6 to 8.

7. The formulation of claim 5 or 6 wherein a radiolytic protectant is present.

8. The formulation of claim 7 wherein the radiolytic protectant is one or more of benzyl alcohol, ascorbic acid, gentisic acid, cysteine, butylated hydroxytoluene (BHT), citric acid, human serum albumin (HSA), glycerol, cysteamine, sulfarem, glutathione, tryptophan, and iodoacetamide.

9. The formulation of claim 8 wherein the radiolytic protectant is the sodium salt of ascorbic acid.

10. The formulation of claim 3 wherein the iodo atom is $^{125}$I, and having as pharmaceutically-acceptable carriers HEPES and acetate buffers, with a radiolytic protectant of ascorbic acid.

11. The formulation of claim 1 wherein less than 10% of unbound iodine is present in the formulation.

* * * * *